United States Patent

Akazawa

Patent Number: 5,607,690

Date of Patent: Mar. 4, 1997

[54] EXTERNAL ANTI-INFLAMMATORY AND ANALGESIC PLASTER PREPARATION

[75] Inventor: Mitsuji Akazawa, Kagawa, Japan

[73] Assignees: Teikoku Seiyaku Co., Ltd., Kagawa, Japan; Altergon S.A., Lugano, Switzerland

[21] Appl. No.: 579,469

[22] Filed: Dec. 27, 1995

Related U.S. Application Data

[63] Continuation of Ser. No. 226,875, Apr. 13, 1994, abandoned.

[30] Foreign Application Priority Data

Apr. 23, 1993 [JP] Japan ................ 5-119246

[51] Int. Cl.$^6$ .................. A61F 13/00
[52] U.S. Cl. .............. 424/443; 424/445; 514/887
[58] Field of Search ............... 424/443, 445; 514/887

[56] References Cited

U.S. PATENT DOCUMENTS 4,948,805  8/1990  Ziggiott, I ................ 514/428

FOREIGN PATENT DOCUMENTS

| 0271709 | 6/1988 | European Pat. Off. | ......... 101/447 |
| 0524582 | 1/1993 | European Pat. Off. | .......... 31/195 |
| 0521393 | 1/1993 | European Pat. Off. | ........... 229/42 |
| 2500751 | 3/1992 | France | ............ 31/205 |
| 57-24308 | 2/1982 | Japan . | |
| 57-81409 | 5/1982 | Japan . | |
| 60-208909 | 10/1985 | Japan . | |
| 61-60608 | 3/1986 | Japan . | |
| 62-181226 | 8/1987 | Japan . | |
| 63-152372 | 6/1988 | Japan . | |
| 9107998 | 6/1991 | WIPO | .............. 15/44 |

OTHER PUBLICATIONS

Drugs under Experimental and Clinical Research; Bioscience, Ediprint, No. 3, 1993; also see p. 94, reference 9.
Chemical Properties—Dissolution Relationship Pharm. Acta. Helv., 66, No. 7, 1991.

*Primary Examiner*—D. Gabrielle Phelan
*Attorney, Agent, or Firm*—Baker & Daniels

[57] ABSTRACT

An external anti-inflammatory and analgesic plaster preparation includes as an active ingredient a salt of diclofenac, 2[(2,6-dichlorophenyl)amino]benzene-acetic acid, with a cyclic organic having the general formula (I):

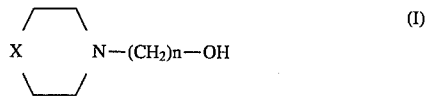

wherein X is a group of the formula —$(CH_2)_m$— in which m is an integer of 0 or 1 and n is an integer of 2 and a pH value of the preparation is adjusted to a range of 7.3 to 9.0.

4 Claims, 2 Drawing Sheets

EXTERNAL ANTI-INFLAMMATORY AND ANALGESIC PLASTER PREPARATION

This is a continuation of application Ser. No. 08/226,875, filed Apr. 13, 1994, now abandoned.

BACKGROUND OF THE INVENTION

1. Field

This invention relates to an external anti-inflammatory and analgesic agent. More particularly, it is concerned with an external anti-inflammatory and analgesic plaster preparation wherein a salt of diclofenac with a cyclic organic base is contained as an active ingredient and release and absorption are remarkably improved.

2. Prior Art

Where various non-steroidal anti-inflammatory and analgesic agents are orally administered, an efficient drug distribution in inflammatory sites is difficult to be achieved and further undesirable side-effects could be produced in gastrointestinal tracts in such diseases developed relatively locally near body surface as arthritis, sarcitis, tenovaginitis and the like.

Accordingly, there have been developed in the field of orthopedics ointments containing various non-steroidal agents in order to avoid systemic side-effects and they have been medicinally supplied as a practical pharmaceutical preparation. Also, there have been proposed plaster preparations as another pharmaceutical preparation having the same efficacy. The plaster preparation could have many advantages not seen in the ointments, such as prolonged effects, precise dosages, simple administration, cooling effects on diseased parts by the free water involved in the base and fixing effects on diseased parts by the preparation. Presently, there have been supplied those plaster preparations containing three sorts of non-steroidal agents, indomethacin, Ketoprofen and flurbiprofen and their usefulness has been appraised. However, these agents have an extremely low solubility in water and thus it is essential to add a specific drug solubilizer or solubilizing agent.

On the other hand, Japanese Patent Kokai Koho No. 63-152372 discloses a salt of diclofenac with an organic cyclic base and a pharmaceutical composition containing same, in which it is reported that the pharmaceutical compositions containing the diclofenac salt are effective as an anti-inflammatory and analgesic for oral administration.

Hitherto, there have been used external anti-inflammatory and analgesic plaster preparations of a diclofenac type containing diclofenac-Na salt as an active ingredient. Since the diclofenac-Na salt has a low solubility to water so that a skin permeability is reduced and therefore, a sufficient pharmacological effect can not be obtained when applied to the skin.

For overcoming such disadvantages, there have been provided various improvements in the external diclofenac-containing plaster preparations. As disclosed in, for example, Japanese Patent Kokai Koho Nos. 57-24308, 57-81409, 60-208909, 61-60608 and 62-181226, there are provided the external anti-inflammatory and analgesic plaster preparations having added a dissolution assistant to raise the solubility of diclofenac Na-salt or having an absorption accelerator to raise the permeability to skin.

However, there are problems that the addition of the dissolution assistant or absorption accelerator results in loss of freedom in a design for preparation and also, the skin subjected to treatment is injured by the dissolution assistant or absorption accelerator used.

Accordingly, an object of the present invention is to provide an anti-inflammatory and analgesic plaster preparation having a sufficient pharmacological effect with good absorption to skin and prolonged effects in respect of the diclofenac-containing anti-inflammatory and analgesic plasters which were regarded as difficult for preparation.

SUMMARY OF THE INVENTION

In accordance with the present invention, there is provided an external anti-inflammatory and analgesic plaster preparation characterized in that said preparation contains a salt of diclofenac, 2[(2,6-dichlorophenyl)amino]benzeneacetic acid, with a cyclic organic base having the general formula (I)

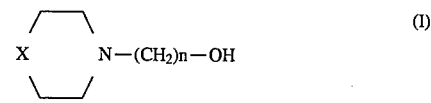

wherein X is a group of the formula —$(CH_2)_m$— in which m is an integer of 0 or 1 and n is an integer of 2 as an active ingredient, a pH adjuster and optionally, a pharmaceutically acceptable ingredient such as thickening agents, humectants, fillers, preservatives and cross-linking agent and also, a pH value of said preparation is adjusted to a range of 7.3 to 9.0.

Also, according to the present invention, there is provoded a process for producing an external anti-inflammatory and analgesic plaster preparation, characterized by subjecting a composition comprising a salt of the above-mentioned diclofenac with a cyclic organic base of general formula (I):

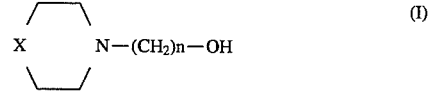

wherein X and n are as defined above as an active ingredient, a pH adjuster and optionally, as a pharmaceutically acceptable ingredient, such as thickening agents, humectants, fillers, preservatives and cross-linking agents, to dissolving or dispersing part or all of the ingredients of said composition in water to obtain a mass;

kneading said mass while adjusting and maintaining a pH thereof at a range of 7.3 to 9.0; and spreading the resulting mass over a support.

DETAILED DESCRIPTION OF THE INVENTION

Figure 1:
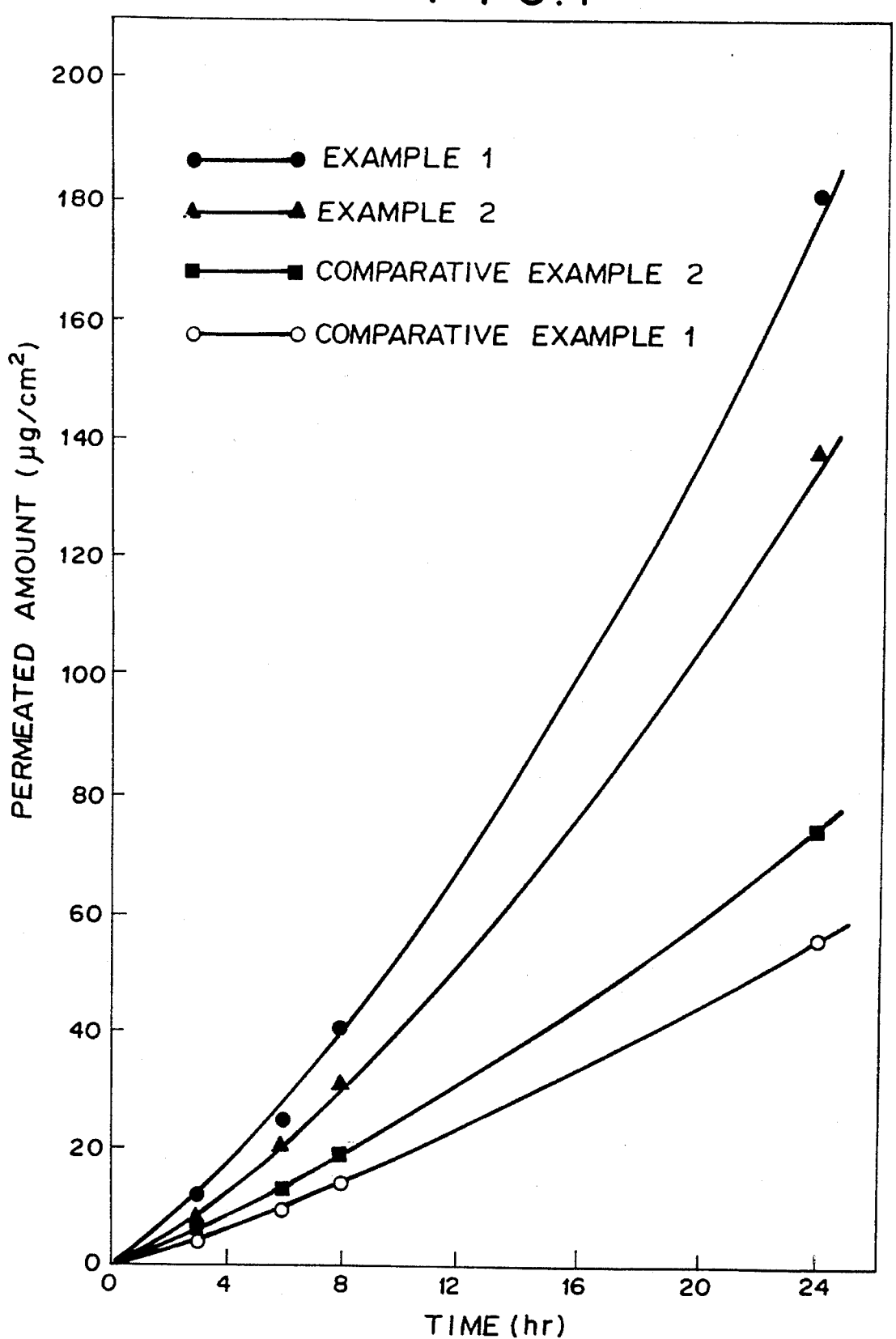
FIG. 1 shows a relationship between the sticking time onto the rat skin and the amount of the durg permeated.

In the external anti-inflammatory and analgesic plaster preparation of the present invention, an amount of the salt of diclofenac with a cyclic organic base, as the active ingredient, to be incorporated in the present plaster preparation may be of a sufficient amount to accomplish the desired therapeutic effect and is not generally critical. Usually, the amount is recommended to be 0.1 to 5.0% by weight, preferably 0.3 to 3.0% by weight. As the cyclic organic base, there may be mentioned, for example, hydroxyethylpyrrolidine, hydroxyethylpiperidine and the like.

It is recommended that a composition for the present plaster preparation may have a pH value of 7.3 to 9, preferably 7.5 to 8.5. At a pH value of less than 7.3, water-insoluble diclofenac crystals may be separated out, while, when a pH value is higher than 9, it may be feared to induce skin irritation. For adjusting a pH value of the composition, there may be used any organic or inorganic acid or base and there is no particular limitation thereto. And, its amount to be employed may vary upon the pH value of the composition and, the sort of a pH adjuster and there is no particular limitation thereto.

Other optional components which may form the present plaster preparation may be thickening agents, humectants, fillers, preservatives, cross-linking agents and others commonly employed in a pharmaceutical field. For instance, one may use as thickening agents polyacrylic acid, sodium polyacrylate, carboxymethylcellulose sodium (CMC Na), polyvinyl alcohol, polyvil pyrrolidone, gelatin and others. The amount used may be within a range of 3 to 30% by weight, preferably 5 to 20% by weight. If the amount is less than 3% by weight, the viscosity of the composition is low so that the composition bleeds to the support and remains on the skin when applied for. On the contrary, if the amount exceeds 30% by weight, the viscosity is highs so that the workability of kneading ingredients or spreading the composition over the support becomes worse.

Examples of humectants include glycerol, propylene glycol, polyethylene glycol, 1,3-butanediol and D-sorbitol solution.

The amount used may be within a range of 5 to 70% by weight, preferably 10 to 60% by weight. If the amount is less than 5% by weight, the humectation effect is not sufficient so that the composition dries rapidly upon application, while with the amount of more than 70% the mixing of ingredients becomes difficult.

Examples of fillers include kaolin and bentonite.

Examples of preservatives are paroxybenzoic acid esters and sorbic acid.

Examples of cross-linking agents are aluminum compounds and calcium compounds. The amount used is, preferably, within a range of 0.01 to 3.0% by weight. If the amount is less than 0.01% by weight, the cross-linking is insufficient so that the heat resistance of the composition is reduced and then, the composition remains on the skin upon application and also, flows out in a conservation bag. On the other hand, if the amount exceeds 3.0% by weight, the rate of cross-linking is too high and thus, the viscosity of the composition is increased so that the workability of kneading and spreading is reduced and then, and adhesiveness of the composition is lowered. Using the foregoing, there are provided the form-retaining property and water-retaining property which are required for the plaster preparation.

The present plaster preparation are obtained by dissolving or dispersing a part of the above components in water and kneading with other components In this connection it is necessary to adjust a pH of the composition not less than 7.3 at the time when the drugs are added and particularly, to adjust and maintain the pH of the composition not less than 7.3 from the beginning to the end of preparation, because diclofenac may be separated out as crystals at a pH value less than 7.3 and the crystals once separated could not be readily dissolved in water even if the pH value may be then increased to exceed 7.3.

In the course of preparation, the addition order of a pH adjuster is not particularly limited. For examples, when an acidic thickening agent is added, a pH is adjusted to 7.3 to 9.0 by addition of an alkaline pH adjuster and thereafter, the drugs are added. At this time the addition order of the thickening agent and pH adjuster is not particularly limited.

Also, when an alkaline thickening agent is added, after addition of the drugs a pH is adjusted by addition of an acidic pH adjuster to 7.3 to 9.0.

At this time, after addition of the thickening agent and pH adjuster to adjust a pH to 7.3 to 9.0, the drugs may be added. Furthermore, after addition of the drugs, any ingredients which do not reduce the pH less than 7.3 may be added.

The present plaster preparation may be finally prepared by blending the salt of diclofenac with a cyclic organic base with the above components, kneading together and spreading the resultant product over a support. There is no particular limitation to spreading methods and a thickness of the plaster preparation, but a therapeutic effect in sealed form may be expected by designing the thickness of the preparation as relatively thicker (e.g., not less than 0.5 mm), together with the effect by the support.

As the support, there is no particular limitation, but there may be desirably employed any flexible materials such as fabrics, non-fabrics, papers, plastic films and laminates thereof, which may easily follow the movement of the affected part.

In the present plaster preparation thus prepared, the active ingredient, the salt of diclofenac with the cyclic organic base, is being stably dissolved in the preparation without separation as crystals by adjusting the pH value to 7.3 to 9, whereby the release and absorption of drug are remarkably improved, the utility rate of the drug is extremely high and superior effects are obtained.

This invention will be more fully described by way of the following examples, but this invention is not to be limited to these examples.

Example 1

| Components | % (w/w) |
|---|---|
| Diclofenac hydroxyethylpyrrolidine (DHEP) | 1.3 |
| Sodiumpolyacrylate | 4 |
| CMC Na | 3 |
| Gelatin | 2 |
| Polyvinyl pyrrolidone | 2 |
| 1,3-Butanediol | 20 |
| D-sorbitol solution | 20 |
| Kaolin | 5 |
| Titanium oxide | 0.5 |
| Aluminum hydroxide | 0.8 |
| Tartaric acid | 0.3 |
| Methylparaben | 0.1 |
| Propylparaben | 0.05 |
| Purified water | q.s. |
| Total | 100 |

To 30 parts of the purified water were added the gelatin and polyvinyl pyrrolidone and they were dissolved by heating at 60° C. To the resulting solution were added the D-sorbitol solution, Kaolin, titanium oxide, methylparaben and propylparaben and a sufficient kneading was carried out. Then, a solution of the sodium polyacrylate, CMC Na and aluminum hydroxide dispersed in the 1.3-butanediol was further added and then a further kneading was carried out. Finally, the DHEP dissolved in the remainder of the purified water was added and the resulting mixture was further kneaded until it became homogeneous. The plaster thus obtained was spread over a non-woven fabric at 1000 g/m². The fabric was stuck on a plastic film and cut into a desired size to prepare a plaster preparation. The preparation as formed had a pH value of 7.9.

Example 2

| Components | % (w/w) |
| --- | --- |
| DHEP | 1.3 |
| Sodium polyacrylate | 2 |
| Polyacrylic acid | 2 |
| CMC Na | 3 |
| Gelatin | 2 |
| Polyvinyl alcohl | 1 |
| Glycerol | 30 |
| Kaolin | 10 |
| Aluminum hydroxide | 0.8 |
| Triethanolamine | 1.5 |
| 1N-Sodium hydroxide | 0.3 |
| Methylparaben | 0.1 |
| Propylparaben | 0.05 |
| Purified water | q.s. |
| Total | 100 |

To 30 parts of the purified water were added the gelatin and polyvinyl alcohol and they were dissolved by heating at 60° C. To the resulting solution were added the poly acrylic acid, D-sorbitol solution, Kaolin, methylparaben, propylparaben and 1N-sodium hydroxide and a sufficient kneading was carried out. Then, a solution of the sodium polyacrylate, CMC Na, triethanolamine and aluminum hydroxide dispersed in the glycerol was further added and then a further kneading was carried out. Finally, the DHEP dissolved in the remainder of the purified water was added and the resulting mixture was further kneaded until it became homogeneous. The plaster thus obtained was spread over a non-woven fabric at 800 g/m². The fabric was stuck on a plastic film and cut into a desired size to prepare a plaster preparation. The preparation as formed had pH value of 7.8.

Example 3

| Components | % (w/w) |
| --- | --- |
| DHEP | 0.65 |
| Sodium polyacrylate | 4 |
| CMC Na | 2.5 |
| Gelatin | 2 |
| Polyvinyl alcohol | 3 |
| Propyleneglycol | 10 |
| D-sorbitol solution | 30 |
| Kaolin | 5 |
| Aluminum acetate | 1.2 |
| Propylparaben | 0.1 |
| Purified water | q.s. |
| Total | 100 |

To 30 parts of the purified water were added the gelatin and polyvinyl alcohol and they were dissolved by heating at 60° C. To the resulting solution were added the D-sorbitol solution, Kaolin and propylparaben and a sufficient kneading was carried out. Then, the DHEP dissolved in the remainder of the purified water was added and a further kneading was carried out. Finally, a solution of the sodium polyacrylate CMC Na and aluminum acetate dispersed in the propylene glycol and the resulting mixture was further kneaded until it became homogeneous. The plaster thus obtained was spread over a non-woven fabric at 1000 g/m². The fabric was stuck on a plastic film and cut into a desired size to prepare a plaster preparation. The preparation as formed had a pH value of 8.5.

Comparative Example 1

| Components | % (w/w) |
| --- | --- |
| Diclofenac Na | 1 |
| Sodium polyacrylate | 4 |
| CMC Na | 3 |
| Gelatin | 2 |
| Polyvinyl pyrrolidone | 2 |
| 1,3-Butanediol | 20 |
| D-sorbitol solution | 20 |
| Kaolin | 5 |
| Titanium oxide | 0.5 |
| Aluminum hydroxide | 0.8 |
| Tartaric acid | 0.3 |
| Methylparaben | 0.1 |
| Propylparaben | 0.05 |
| Purified water | q.s. |
| Total | 100 |

Following the same procedure as described in Example 1 except that diclofenac Na was employed instead of the DHEP, there was formed an external plaster preparation. The preparation as formed had a pH value of 8.0.

Comparative Example 2

| Components | % (w/w) |
| --- | --- |
| DHEP | 1.3 |
| Sodium polyacrylate | 2 |
| Polyacrylic acid | 2 |
| CMC Na | 3 |
| Gelatin | 2 |
| Polyvinyl alcohol | 1 |
| Glycerol | 30 |
| Kaolin | 10 |
| Aluminum hydroxide | 0.4 |
| Tartaric acid | 0.3 |
| Methylparaben | 0.1 |
| Propylparaben | 0.05 |
| Purified water | q.s. |
| Total | 100 |

To 30 parts of the purified water were added the gelatin and polyvinyl alcohol and they were dissolved by heating at 60° C. To the resulting solution were added the polyacrylic acid, D-sorbitol solution, Kaolin, methylparaben, propylparaben and tartaric acid and a sufficient kneading was carried out. Then, a solution of the sodium polyacrylate, CMC Na and aluminum hydroxide dispersed in the glycerol was added and a further kneading was carried out. Finally, the DHEP dissolved in the remainder of the purified water was added and a further kneading was carried out until it became homogeneous. The plaster thus obtained was spread over a non-woven fabric at 1000 g/m². The fabric was stuck on a plastic film and cut into a desired size to prepare a plaster preparation. The preparation as formed had a pH value of 6.8.

TEST EXAMPLE 1

The skin excised from the rat abdomen was placed into Franz diffusion cell, while each of the test preparation obtained by Examples 1 and 2 and Comparative Examples 1 and 2 and was punched into a circle with a diameter of 1.7 cm, which was then put on the rat skin (n=7). An amount of the drug permeated through the rat skin after a given time was determined by HPLC using a phosphate buffer at pH 7.0 on a receptor side. The results are shown in FIG. 1.

As apparent from FIG. 1, the present plaster preparation showed a far better skin permeabilily as compared with the plaster preparation of diclofenac Na incorporated into the same composition. Also, the plaster preparation (Comparative Example 2) having a pH value of 6.8, thought it contained the same drug as used in the present plaster preparation, apparently showed an inferior skin permeabilily to that of the present plaster preparation.

TEST EXAMPLE 2

For evaluation of an analgesic effect of the plaster preparation, a carrageenin edema rate was measured as follows:

Wistar rats weighing 150 to 180 g were used, a group consisting of 10 animals. A volume of right hind leg of each rat was measured prior to the administration of the drug. Thereafter, each of the plaster preparations obtained by Examples 1 and 3 and Comparative Example 1 was cut to a sheet with 3×4 and then applied. After 4 hours from the administration, the plaster preparation was peeled off and immediately 0.1 of a 1 w/v% suspension of carrageenin was injected subcutaneously into the planter of rat. Volumes of leg were measured at 2, 3 and 4 hours after the injection and an edema rate was calculated from the leg volume prior to the carrageenin injection according to the following equation:

$$\text{Edema rate (\%)} = \frac{V - V_0}{V_0} \times 100$$

where
$V_0$: Leg volume prior to the carrageenin injection.
$V$: Leg volume at every measuring time after the carrageenin injection.

Figure 2:
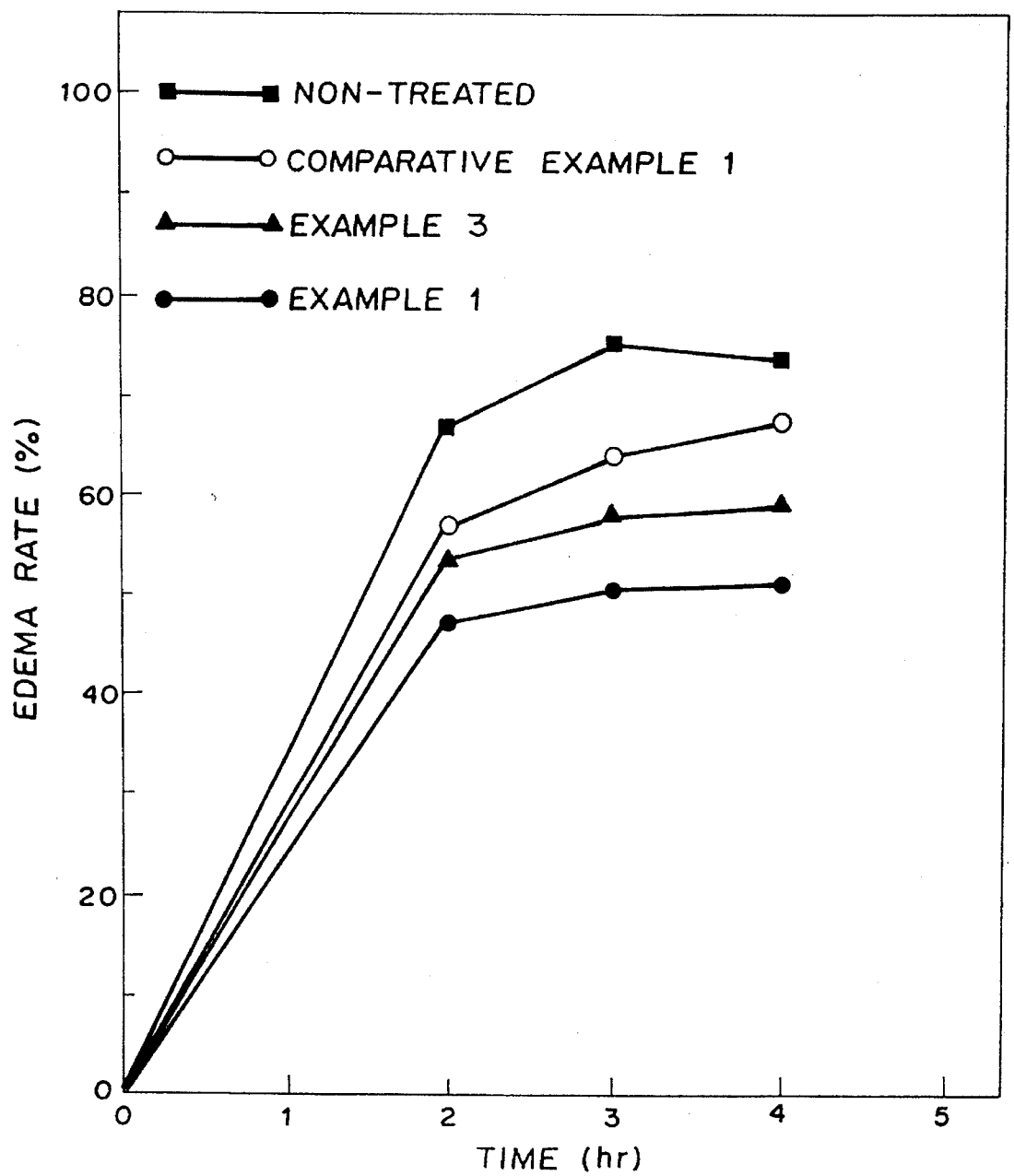
FIG. 2 shows a relationship between the times lapsed after caargeenin injection and the edema rate in percent of the rat planter.

The results are shown in FIG. 2.

As apparent from FIG. 2, the present plaster preparation showed a higher edema-inhibitory effect as compared with the conventional plaster preparation containing a diclofenac derivative.

TEST EXAMPLE 3

In order to determine whether or not there may be found any crystals of diclofenac in plaster preparations, a polarizing microscopic observation was carried out on the test preparations immediately after prepared in Examples 1, 2 and 3 and Comparative Example 2 and after storage for 24 hours at 5° C. and room temperature.

The results are shown in Table 1.

TABLE 1

|  | Immediately After Preparation | 5° C. 24 Hours | Room Temp. 24 Hours |
|---|---|---|---|
| Example 1 | Not observed at all | Not observed at all | Not observed at all |
| Example 2 | Not observed at all | Not observed at all | Not observed at all |

TABLE 1-continued

|  | Immediately After Preparation | 5° C. 24 Hours | Room Temp. 24 Hours |
|---|---|---|---|
| Example 3 | Not observed at all | Not observed at all | Not observed at all |
| Comparative Example 2 | Slightly observed | Many observed | Many observed |

As apparent from Table 1 above, any separation of crystals was not observed at all in the present plaster preparation. However, separation of many crystals was observed after one day in the preparation obtained by Comparative Example 2 having a lower pH value.

What is claimed is:

1. An external anti-inflammatory and analgesic plaster preparation comprising a salt of diclofenac, 2[(2,6-dichlorophenyl)amino]benzene-acetic acid and a cyclic organic base as an active ingredient, said cyclic organic base comprising hydroxyethylpyrrolidine or hydroxyethylpiperidine, a pH adjuster and optionally, pharmaceutically acceptable thickening agents, humectants, fillers, preservatives and cross-linking agents, wherein a pH value of said preparation is adjusted to a range of 7.3 to 9.0.

2. The external plaster preparation of claim 1 wherein the pH value of the preparation is within a range of 7.5 to 8.5.

3. A process for producing an external anti-inflammatory and analgesic plaster preparation, comprising subjecting a composition comprising a salt of diclofenac, 2[2,6-dichlorophenyl)amino]benzene-acetic acid with a cyclic organic base as an active ingredient, said cyclic organic base comprising hydroxyethylpyrrolidine or hydroxyethylpiperidine, a pH adjuster and optionally, pharmaceutically acceptable thickening agents, humectants, fillers, preservatives and cross-linking agents to the steps of incorporating each ingredient, dissolving or dispersing a part or all of the ingredients in water, and kneading one ingredient with other ingredients while adjusting and maintaining a pH of the composition at a range of 7.3 to 9.0 during the step of preparation and then, spreading the resulting product over a support.

4. An external anti-inflammatory and analgesic plaster comprising:

a preparation containing a salt of diclofenac, 2[(2,6-dichlorophenyl)amino]benzene-acetic acid with a cyclic organic base as an active ingredient, said cyclic organic base comprising hydroxyethylpyrrolidine or hydroxyethylpiperidine; a pH adjuster; pharmaceutically acceptable ingredients comprising a thickening agent; a humectant; a filler, a preservative and a cross-linking agent, wherein a pH value of the said preparation is adjusted to a range of 7.3 to 9.0; and a support on which said preparation is spread.

* * * * *

UNITED STATES PATENT AND TRADEMARK OFFICE
CERTIFICATE OF CORRECTION

PATENT NO. : 5,607,690
DATED : March 4, 1997
INVENTOR(S) : Mitsuji Akazawa

It is certified that error appears in the above-indentified patent and that said Letters Patent is hereby corrected as shown below:

Claim 3, column 8, line 30, after "diclofenac,", replace "2[2,6-dichlo-" with -- 2[(2,6-dichlo- --.

Signed and Sealed this

Twenty-eighth Day of October, 1997

Attest:

BRUCE LEHMAN

*Attesting Officer*  *Commissioner of Patents and Trademarks*